United States Patent
Wolf et al.

(10) Patent No.: US 7,190,888 B2
(45) Date of Patent: Mar. 13, 2007

(54) METHOD OF ADJUSTING THE VAPORIZATION RATE OF A DEVICE

(75) Inventors: Lawrence R. Wolf, Avilla, IN (US); Robert G. Cox, Goshen, IN (US)

(73) Assignee: Dekko Technologies, Inc., North Webster, IN (US)

( * ) Notice: Subject to any disclaimer, the term of this patent is extended or adjusted under 35 U.S.C. 154(b) by 0 days.

(21) Appl. No.: 11/150,399

(22) Filed: Jun. 9, 2005

(65) Prior Publication Data

US 2005/0276584 A1    Dec. 15, 2005

Related U.S. Application Data

(60) Provisional application No. 60/578,605, filed on Jun. 10, 2004.

(51) Int. Cl.
    *F24H 6/08*    (2006.01)

(52) U.S. Cl. .................................. 392/395; 392/386
(58) Field of Classification Search .................. None
    See application file for complete search history.

(56) References Cited

U.S. PATENT DOCUMENTS

| 6,078,728 | A | * | 6/2000 | O'Rourke et al. | .......... | 392/390 |
| 6,278,840 | B1 | * | 8/2001 | Basaganas Millan | ....... | 392/390 |
| 6,285,830 | B1 | * | 9/2001 | Basaganas Millan | ....... | 392/395 |
| 6,782,194 | B2 | * | 8/2004 | Schneiderbauer | ........... | 392/395 |
| 2005/0180736 | A1 | * | 8/2005 | Zobele | ...................... | 392/395 |

* cited by examiner

*Primary Examiner*—Thor S. Campbell
(74) *Attorney, Agent, or Firm*—Taylor & Aust, P.C.

(57) ABSTRACT

A vaporization device including a housing, a container, a wick, a heating element and an adjustment mechanism. The wick is fixed to the container and extends therefrom. The heating element is positioned in the housing proximate a portion of the wick. The adjustment mechanism interconnects the container with the housing.

20 Claims, 3 Drawing Sheets

METHOD OF ADJUSTING THE VAPORIZATION RATE OF A DEVICE

CROSS-REFERENCE TO RELATED APPLICATIONS

This is a non-provisional application based upon U.S. provisional patent application Ser. No. 60/578,605, entitled "METHOD OF ADJUSTING THE VAPORIZATION OF A DEVICE", filed Jun. 10, 2004.

BACKGROUND OF THE INVENTION

1. Field of the Invention

The present invention relates to wicked vaporization systems, and, more particularly, to wicked vaporization systems using a heating element.

2. Description of the Related Art

An electrically heated chemical delivery system, which is connectable with an electrical receptacle, is known. For example, it is known to provide a housing, which directly carries a pair of terminals, which extend therefrom and may be plugged into a conventional 115-volt electrical receptacle. The electrical terminals are electrically connected to a heater disposed within the body of the delivery system. A heat-actuated chemical is disposed within the body and releases its gasses into the ambient environment with heat accelerating the release.

One method used to alter the amount of vaporizable material that is released in the environment is to control the airflow around the heating element. Controlling the airflow requires adjustable elements in the housing to alter the airflow that passes by the vaporizable material.

Another method of controlling the vaporization of the vaporizable material is to alter the heat supplied by way of the heating element. This requires control electronics, which add substantial cost to the assembly.

What is needed in the art is a way to adjust the vaporization rate in a simple cost effective manner.

SUMMARY OF THE INVENTION

The present invention provides a vaporization system that adjusts a vaporization rate of a vaporizable material without altering the airflow through the system.

The invention comprises, in one form thereof, a vaporization device including a housing, a container, a wick, a heating element and an adjustment mechanism. The wick is fixed to the container and extends therefrom. The heating element is positioned in the housing proximate a portion of the wick. The adjustment mechanism interconnects the container with the housing.

An advantage of the present invention is that the vaporization rate of material in the wick is adjusted without altering the power supplied to a resistive heater.

Another advantage of the present invention is that the vaporization rate of the vaporizable material in the wick is adjusted without altering airflow through the vaporization device.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
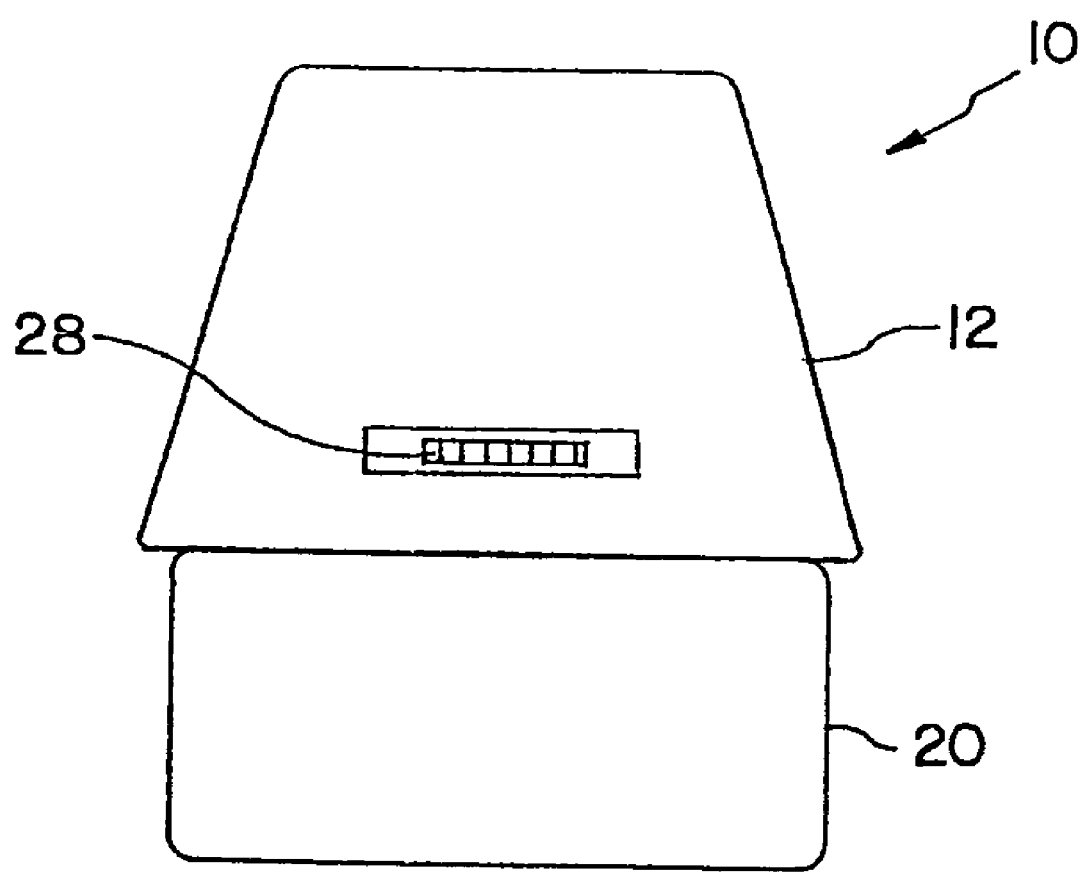
FIG. 1 is a side view of an embodiment of a vaporization device of the present invention.
Figure 2:
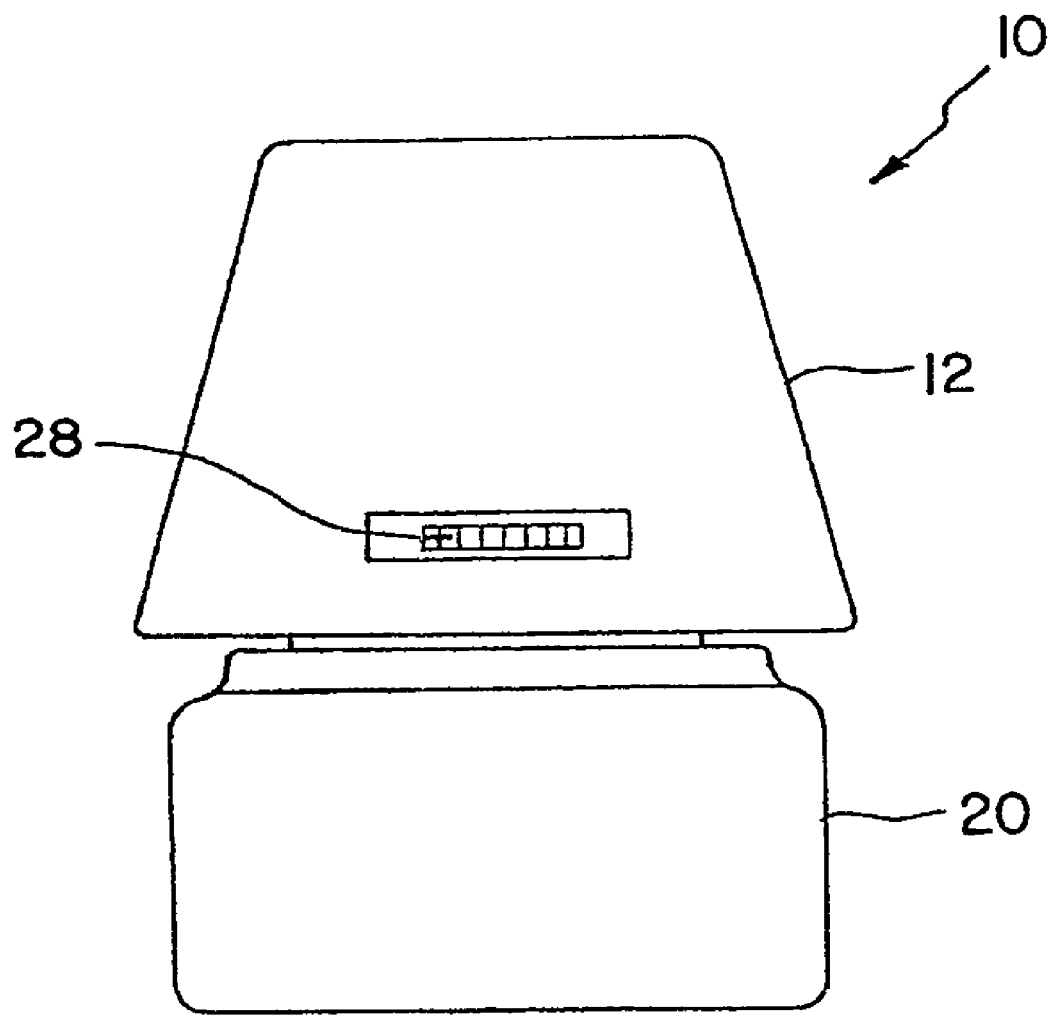
FIG. 2 is another side view of the vaporization device of FIG. 1.
Figure 3:
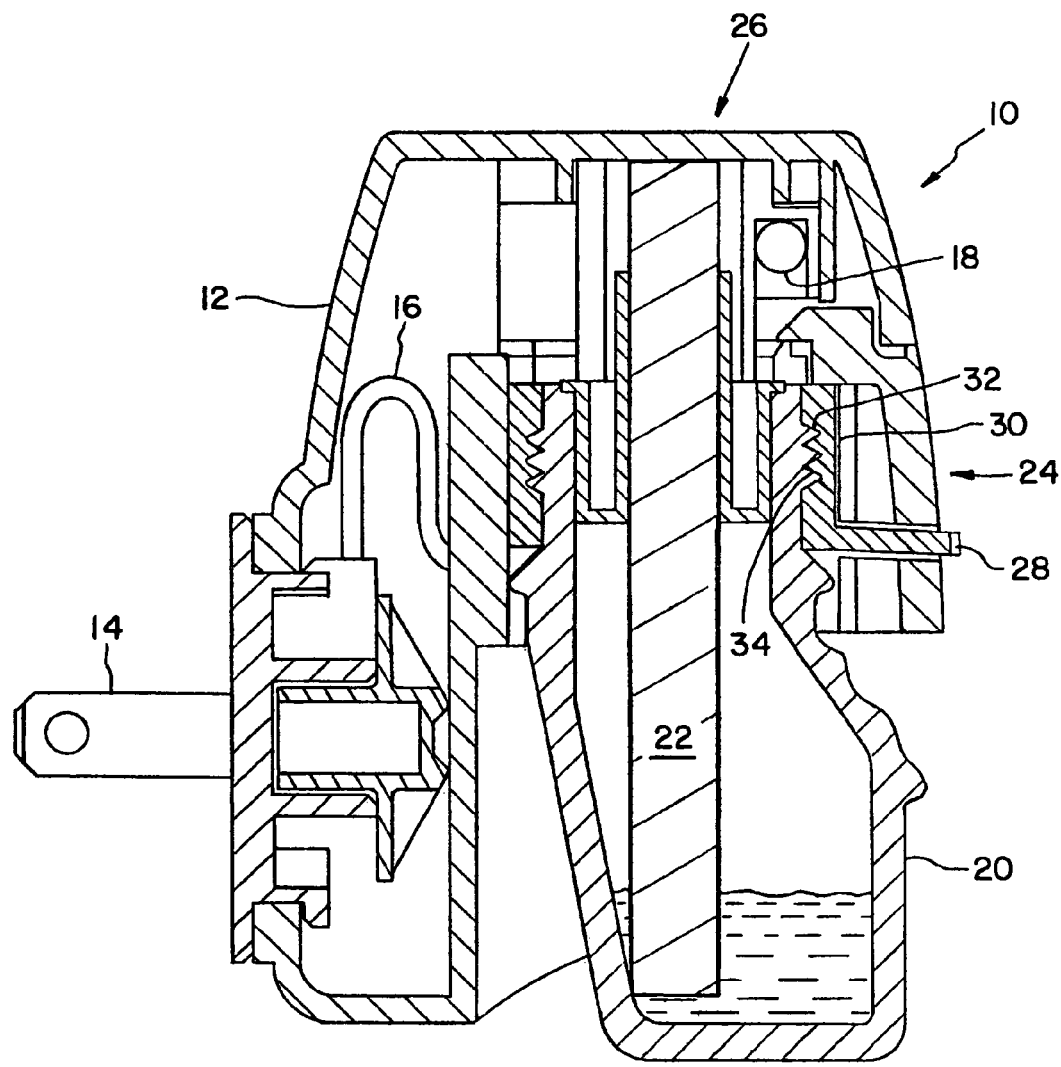
FIG. 3 is a cross-sectional view of the vaporization device of FIGS. 1 and 2.

Referring now to the drawings, and more particularly to FIGS. 1–3, there is shown a vaporization device 10, which generally includes a housing 12, electrical terminals 14, wires 16, an electrical heater 18, a container 20, a wick 22 and an adjustment mechanism 24. Housing 12 includes routing space for containing electrical terminals 14 and conveying wires 16 to an electrical connection with electrical heater 18. Wick 22 routed within container 20 to contact a supply of vaporizable material and wick 22 is affixed to container 20. A predetermined portion of wick 22 extends from container 20 and a portion is immersed in the vaporizable material contained within container 20. The vaporizable material may be in the form of a fluid fragrance, an insecticide, a medicine or other material that is desirable to be released in the air. The vaporizable material wicks up wick 22 from container 20 and is in contact with ambient air. In order to accelerate the vaporization of the vaporizable material, electrical heater 18 transfers heat to a portion of wick 22. The amount of heat transferred from electrical heater 18 to wick 22 is dependent upon the amount of wick 22 that is proximate to electrical heater 18. An intermediate heat transfer device can be shaped to be proximate to, or in contact with, wick 22 to thereby define a heat transfer profile to wick 22. The amount of wick 22 that is subject to heat transfer from electrical heater 18 effects the vaporization rate of the vaporizable material contained in wick 22.

Housing 12 includes a wick opening 26 through which ambient air, and some of the vaporizable material carried thereby, can proceed. Housing 12 includes other openings in which air is allowed to enter air pathways that are unaffected by the position of adjustment mechanism 24.

Adjustment mechanism 24 includes an adjustment knob 28 that is connected to an adjustment sleeve 30. Adjustment sleeve 30 is captivated within housing 12 and is rotatable therein. Adjustment sleeve 30 additionally includes a threaded portion 32, which interacts with a threaded portion 34 of container 20 to effect the movement of container 20 relative to housing 12.

As adjustment knob 28 is rotated it causes adjustment sleeve 30 to rotate within housing 12 and threaded portions 32 and 34 co-act to cause container 20 to move either toward or away from housing 12 depending upon the direction of movement of adjustment knob 28. When electrical terminals 14 are plugged into an electrical receptacle that is arranged in a generally vertically manner, then the movement of container 20 relative to housing 12 is in a substantially vertical direction. Container 20 includes a keying feature, which prevents container 20 from rotating when adjustment sleeve 30 rotates therearound.

When container 20 is positioned as shown in FIG. 1, heat transfer from electrical heater 18 to wick 22 is maximized, thereby causing the vaporization rate of the vaporizable material to be maximized. When container 20 is moved away from housing 12, as shown in FIG. 2, the heat transfer from electrical heater 18 to wick 22 is reduced thereby causing the vaporization of the vaporizable material to be at a reduced rate as compared to the position of container 20 that is illustrated in FIG. 1.

Although electrical heater 18 is shown as substantially perpendicular to wick 22, in FIG. 3, other orientations of heating element 18 are also contemplated, which may co-act with the movement of wick 22 relative thereto. Additionally both linear and non-linear heating elements 18 are contemplated for use in vaporization device 10 in order to change the rate of increase of heat transfer to wick 22 as wick 22 moves relative to electrical heater 18.

Advantageously, the present invention alters the heat flow from electrical heater 18 to wick 22, thereby varying the temperature of wick 22. The vaporization of chemicals that are contained in wick 22 increases with the temperature of wick 22. The present invention simply adjusts the heat transfer by altering the relative position of wick 22 to electrical heater 18, rather than using another device to adjust the power supplied to electrical heater 18. This simple solution reduces the cost involved in having an adjustable vaporization rate device as compared with other methods of adjustment. The adjustment of container 20 relative to housing 12 does not alter the airflow velocity or volume of air that flows through vaporization device 10, since air pathways therein are not altered by adjustment mechanism 24.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A vaporization device, comprising:
   a housing;
   a container;
   a wick fixed to said container and extending therefrom;
   a heating element positioned in said housing proximate a portion of said wick; and
   an adjustment mechanism interconnecting said container to said housing, said container being constrained to not rotate relative to said housing when said adjustment mechanism is adjusted.

2. The vaporization device of claim 1, wherein said adjustment mechanism moves said container, thereby moving said wick relative to said heating element to alter a vaporization rate of a vaporizable material in said wick.

3. The vaporization device of claim 2, wherein said vaporizable material is wicked from said container by said wick.

4. The vaporization device of claim 2, wherein said adjustment mechanism includes:
   a knob extending from said housing; and
   a sleeve rotationally captivated in said housing.

5. The vaporization device of claim 4, wherein said sleeve includes a threaded portion and said container includes a threaded portion that co-acts with said threaded portion of said sleeve to effect a movement of said container when said knob is moved.

6. The vaporization device of claim 5, wherein said movement is substantially in a vertical direction.

7. The vaporization device of claim 2, wherein said adjustment mechanism does not alter an airflow volume through the vaporization device.

8. A vaporization device, comprising:
   a housing including a heating element;
   a container including a wick extending therefrom, said heating element transferring heat to said wick; and
   an adjustment mechanism interconnecting said container a variable distance from said housing, said container being constrained to not rotate relative to said housing when said adjustment mechanism is adjusted.

9. The vaporization device of claim 8, wherein said adjustment mechanism moves said container, thereby moving said wick relative to said heating element to alter a vaporization rate of a vaporizable material in said wick.

10. The vaporization device of claim 9, wherein said vaporizable material is wicked from said container by said wick.

11. The vaporization device of claim 9, wherein said adjustment mechanism includes:
    a knob extending from said housing; and
    a sleeve rotationally captivated in said housing.

12. The vaporization device of claim 11, wherein said sleeve includes a threaded portion and said container includes a threaded portion that co-acts with said threaded portion of said sleeve to effect a movement of said container when said knob is moved.

13. The vaporization device of claim 12, wherein said movement is substantially in a vertical direction.

14. The vaporization device of claim 9, wherein said adjustment mechanism does not alter an airflow volume through the vaporization device.

15. A method of altering a vaporization rate of a vaporizable material from a wick, comprising the step of moving the wick and a container from which the wick extends one of toward and away from a housing having a heating element fixed therein, said container being constrained to not rotate relative to said housing when said container moves one of toward and away from said housing.

16. The method of claim 15, further comprising the step of rotating a knob thereby executing said moving step.

17. The method of claim 16, wherein said knob is connected to a sleeve that is rotatably captive in said housing.

18. The method of claim 17, wherein said container does not rotate as said rotating step is executed.

19. The method of claim 18, wherein said container is threadedly engaged with said sleeve.

20. The method of claim 15, wherein said moving step does not alter either a volume or velocity of an airflow through said housing.

* * * * *